United States Patent [19]
Takamatsu et al.

[11] Patent Number: 6,100,415
[45] Date of Patent: Aug. 8, 2000

[54] PURIFIED ALKOXIDE AND PROCESS FOR PURIFYING CRUDE ALKOXIDE

[75] Inventors: Yukichi Takamatsu; Takeo Yoneyama; Yoshiyasu Ishihama, all of Kanagawa-ken, Japan

[73] Assignee: Japan Pionics Co., Ltd., Tokyo, Japan

[21] Appl. No.: 09/267,791

[22] Filed: Mar. 15, 1999

[30] Foreign Application Priority Data

Mar. 16, 1998 [JP] Japan .................................. 10-085014

[51] Int. Cl.[7] ................................ C07F 9/00; C07F 7/00; C07F 5/06
[52] U.S. Cl. ................................ 556/42; 556/54; 556/76; 556/81; 556/182; 556/400; 568/8; 568/14
[58] Field of Search .................................. 556/42, 54, 76, 556/81, 182, 400; 568/8, 14

[56] References Cited

U.S. PATENT DOCUMENTS 5,575,901  11/1996  Hulme et al. ........................... 205/413

FOREIGN PATENT DOCUMENTS 0667200   8/1995   European Pat. Off. .
63-91339  4/1988   Japan .
3-291247  12/1991  Japan .

*Primary Examiner*—Porfirio Nazario-Gonzalez
*Attorney, Agent, or Firm*—Oblon, Spivak, McClelland, Maier & Neustadt, P.C.

[57] ABSTRACT

A purified alkoxide from which volatile impurities causing polymerization and degradation of the alkoxide are removed to extremely low concentrations. The purified alkoxide can be obtained by distilling a crude alkoxide and stripping the distilled liquid alkoxide by applying ultrasonic vibration while passing an inert gas through the liquid alkoxide. A high quality thin insulating film excellent in flatness with few defects such as voids can be obtained by using the purified alkoxide of the present invention as a CVD material.

10 Claims, 1 Drawing Sheet

PURIFIED ALKOXIDE AND PROCESS FOR PURIFYING CRUDE ALKOXIDE

FIELD OF THE INVENTION

The present invention relates to a purified alkoxide used for applications requiring a high purity such as a semiconductor production, and a process for purifying a crude alkoxide, and more specifically, to a high-purity alkoxide obtained by removing impurities such as alcohols, polymers of the alkoxide, water, halogens, hydrogen halides, oxygen and carbon dioxide from the crude alkoxide, and a process for purifying the crude alkoxide by removing the above impurities.

BACKGROUND OF THE INVENTION

Thin insulating films of semiconductor devices may include a gate insulating film such as $SiO_2$ film, a capacitor insulating film such as $Si_3N_4$ film, a layer-insulating film such as PSG (phosphorus-silicon glass) film and BPSG (boron-phosphorus-silicon glass), etc. As the CVD material for forming these thin films, gaseous materials such as $SiH_4$, $NH_3$, $PH_3$ and $B_2H_6$ have heretofore been used.

The recent trend of making an electronic device into a three-dimensional structure and forming circuits on increased number of layers of a laminated structure requires a thin insulating film of even more improved flatness. In this circumstance, an alkoxide has come to be used as a liquid CVD material due to its ability of forming a high-quality thin film with little defect such as void. For example, tetraethoxysilicon ($Si(OC_2H_5)_4$) is practically used as a CVD material for forming $SiO_2$ film and trimethoxyboron ($B(OCH3)_3$), trimethoxyphosphorus ($P(OCH_3)_3$), etc. are practically used as a CVD material or forming BPSG film.

In addition, $Ta_2O_5$ film, $HfO_2$ film, etc. having a dielectric constant several times as high as that of $SiO_2$ film have been recently developed. The $Ta_2O_5$ film has been used as the capacitor insulating film. As the CVD material for these thin films, used are pentaethoxytantalum ($Ta(OC_2H_5)_5$) and tetra-t-butoxyhafnium ($Hf(OC(CH_3)_3)_4$).

An extremely high purity is required for the liquid CVD materials such as the alkoxide to form a high-quality thin insulating film. Therefore, impurities such as alcohols, polymers of alkoxides and water should be removed from the alkoxide by distillation before being used as the CVD materiel.

However, when a liquid alkoxide distilled by a conventional process is used as the liquid CVD material, a thin insulating film having a sufficiently high quality cannot be obtained although defects such as voids in the deposited thin insulating film decreases in comparison with those in a thin insulating film deposited by using a gaseous CVD material. This failure in obtaining a sufficiently high quality is assumed that the vapor phase deposition is adversely affected by the volatile impurities such as halogens, hydrogen halides, oxygen and carbon dioxide present in the alkoxide and the polymers and degradation products of the alkoxide formed by heating for vaporization. However, no method has been reported in successfully eliminating the above problem.

SUMMARY OF THE INVENTION

Accordingly, an object of the present invention is to provide a purified alkoxide capable of forming a high-quality insulating film and a process for purifying an alkoxide.

As a result of intensive studies in view of the object, the inventors have found that the alkoxide is likely to cause polymerization in the presence of oxygen, that the volatile impurities such as halogens, hydrogen halides, oxygen, carbon dioxide, etc. dissolved in a liquid alkoxide cannot be sufficiently removed only by distillation, and that the volatile impurities dissolved in the liquid alkoxide in trace amounts can be removed almost completely by applying ultrasonic vibration to the liquid alkoxide while bubbling an inert gas into the liquid alkoxide. The present invention has been accomplished based on the finding.

Thus, in a first aspect of the present invention, there is provided a purified alkoxide having a concentration of residual oxygen of 0.1 ppm or less.

In a second aspect of the present invention, there is provided a process for purifying a crude alkoxide, comprising a step of distilling the crude alkoxide and a step of stripping the distilled liquid alkoxide by applying ultrasonic vibration while introducing an inert gas into the alkoxide.

DESCRIPTION OF THE PREFERRED EMBODIMENTS

Figure 1:
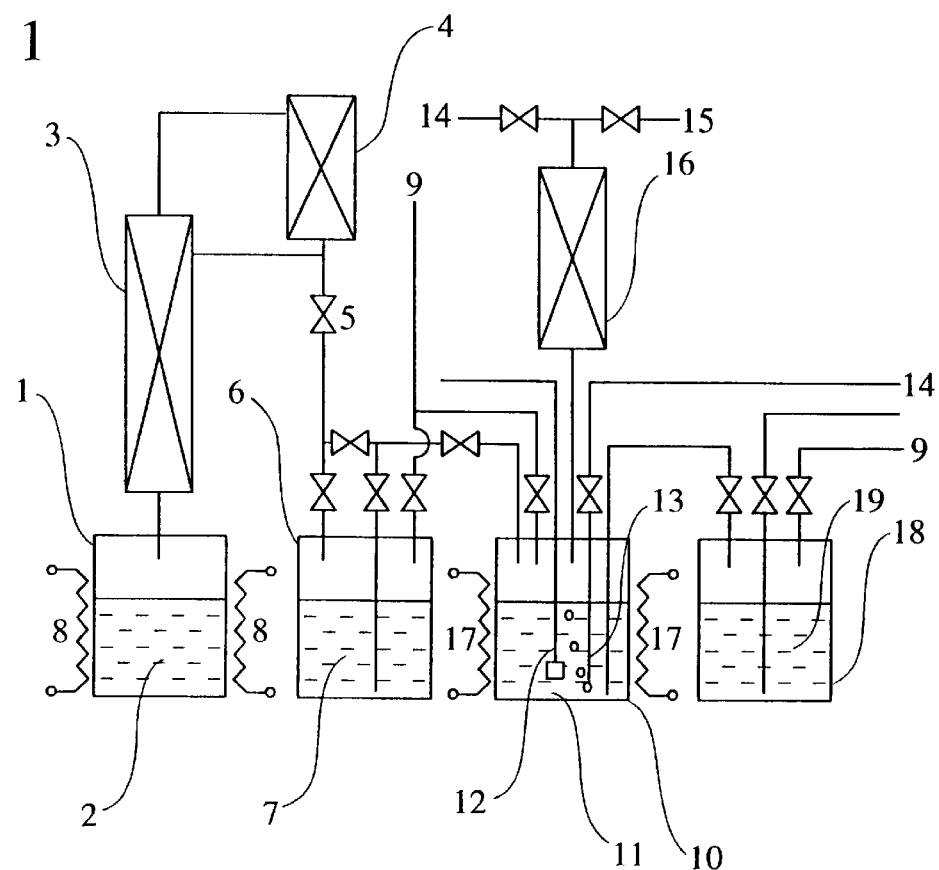
FIG. 1 is a schematic illustration showing an apparatus used in the process for purifying an alkoxide of the present invention.

The present invention relates to an alkoxide used for applications requiring a high purity such as semiconductor production, etc.

The alkoxide referred to in the present invention is a compound obtained by replacing hydrogen in a hydroxyl group of an alcohol with a metal and is used as a liquid CVD material for forming a thin insulating film in the process of producing semiconductors. The alkoxide has the following general formula represented by

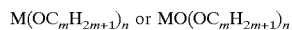

wherein M represents a metal, m represents an integer of 1 to 4 and n represents an integer of 3 to 5. Specifically, the alkoxide referred to herein may include tetraisopropoxytitanium ($Ti(OCH(CH_3)_2)_4$), tetra-n-propoxytitanium ($Ti(OC_3H_7)_4$), tetra-t-butoxyzirconium ($Zr(OC(CH_3)_3)_4$), tetra-n-butoxyzirconium ($Zr(OC_4H_9)_4$), tetra-t-butoxyhafnium ($Hf(OC(CH_3)_3)_4$), tetramethoxyvanadium ($V(OCH_3)_4$), trimethoxyvanadyl oxide ($VO(OCH3)_3$), pentaethoxyniobium ($Nb(OC_2H_5)_5$), pentaethoxytantalum ($Ta(OC_2H_5)_5$), trimethoxyboron ($B(OCH_3)_3$), triisopropoxyaluminum ($Al(OCH(CH_3)_2)_3$), tetraethoxysilicon ($Si(OC_2H_5)_4$), tetraethoxygermanium ($Ge(OC_2H_5)_4$), tetramethoxytin ($Sn(OCH_3)_4$), trimethoxyphosphorus ($P(OCH_3)_3$), trimethoxyphosphine oxide ($PO(OCH_3)_3$), triethoxyarsenic ($As(OC_2H_5)_3$) and triethoxyantimony ($Sb(OC_2H_5)_3$).

The purified alkoxide and the process of purifying a crude alkoxide of the present invention will be described in detail.

The purified alkoxide of the present invention is obtained by distilling a crude alkoxide and stripping a liquid of the distilled alkoxide by applying ultrasonic vibration while passing an inert gas through the liquid alkoxide. The alkoxide thus purified has a concentration of residual oxygen of 0.1 ppm or less.

The process for obtaining the purified alkoxide of the present invention is characterized by a step of distilling a crude alkoxide and a step of stripping a liquid of the distilled alkoxide by applying ultrasonic vibration while passing an inert gas through the liquid alkoxide.

The crude alkoxide contains the impurities such as alcohols, polymers of the alkoxide, water, halogens, hydrogen halides, oxygen, carbon dioxide. For example, the crude alkoxide generally contains oxygen, halogens, hydrogen halides, etc. in respective amounts of at least several hundred ppm.

In the purification process of the present invention, the low-boiling point impurities such as alcohols and high-boiling point impurities such as polymers of the alkoxide are removed from the crude alkoxide by distillation. Any distillation method may be used in the present invention so long as the impurities are efficiently removed without causing decomposition or degradation of the alkoxide. It is preferable that the distillation is conducted under a reduced pressure or under ordinary pressure because distillation under an increased pressure requires a high temperature and the alkoxide is likely polymerized, decomposed or degraded.

It is impossible to completely remove the volatile impurities such as halogens, hydrogen halides, oxygen and carbon dioxide contained in a liquid crude alkoxide by distillation. For example, oxygen remains in a distilled alkoxide in an amount of about several hundreds ppm. When the alkoxide, i.e., $M(OC_mH_{2m+1})_n$ or $MO(OC_mH_{2m+1})_n$, is heated in the presence of oxygen as the impurity, polymers of the alkoxide, i.e., $(C_mH_{2m+1}O)_nMOM(OC_mH_{2m+1})_n)$, etc., are formed. In the formula, M, m and n are as defined above. When the polymers are present in the alkoxide vapor as impurities, defects occur in a thin film being deposited during the production of semiconductors.

To remove such impurities almost completely, the stripping step of the alkoxide is employed in the present invention. The stripping is conducted by placing the distilled alkoxide into a stripping vessel equipped with an ultrasonic vibrator and applying ultrasonic vibration to the liquid alkoxide while introducing an inert gas such as nitrogen, argon and helium into the liquid alkoxide so as to form fine bubbles of the inert gas. By the stripping, the concentration of oxygen in the liquid alkoxide can be reduced, for example, to 0.1 ppm or less. When the stripping is carried out without applying the ultrasonic vibration, the volatile impurities cannot be sufficiently removed.

The shape of the vessel used for the stripping is preferably selected so that the liquid alkoxide introduced therein has a depth sufficient for bringing the inert gas into well contact with the alkoxide during the inert gas bubbles up toward the liquid surface. Further, the vessel is preferably made into a shape capable of making the liquid alkoxide efficiently stirred by the inert gas passing therethrough. It is also preferable that a nozzle through which the inert gas is injected in to the alkoxide has a perforated structure so that fine bubbles of the inert gas are dispersed throughout the alkoxide.

The material for the portion of the stripping vessel and the attachments such as the ultrasonic vibrator exposed to the alkoxide is not particularly limited so long as the above object can be achieved. Usually, a corrosion resistant metal such as tantalum, titanium, electrolytically polished SUS 316 and electrolytically polished SUS 316L is preferably used in view of providing the corrosion resistance and preventing the leak of gas from the vessel and a decrease in purity of the alkoxide by possible elution of impurities from the material.

The stripping is usually conducted at a temperature of room temperature to 80° C. and preferably 40 to 50° C. for 10 minutes to 10 hours. The frequency of the ultrasonic vibration being applied is preferably 30 to 200 kHz and the output power of the ultrasonic vibration is preferably 0.05 to 100 W per 1-liter alkoxide. Ultrasonic vibration of 50 to 60 kHz with 0.5 to 10 W output power per 1-liter alkoxide is more preferred.

As the inert gas introduced into the alkoxide for the stripping, a highly purified gas is used to prevent contamination of the alkoxide with impurities in the inert gas. Although the amount of the inert gas is not particularly limited, the amount is preferred to be selected so that the stripping effect is sufficiently obtained and sudden or violent splashing does not take place at the surface of the alkoxide. The amount is suitably selected also in accordance with the size and the shape of the stripping vessel and the depth of the alkoxide, and preferably 0.05 to 5 cc per unit area ($cm^2$) of a plane perpendicular to the depth direction of the alkoxide.

At an upper portion of the stripping vessel, a reflux condenser is preferably disposed. The reflux condenser is cooled suitably in accordance with the vapor pressure and the melting point of the alkoxide to recover the vaporized alkoxide accompanied by the inert gas during the stripping operation.

In the distillation step, a portion of a low-boiling point impurity separated from the alkoxide is dissolved again in the alkoxide during the vaporized alkoxide is condensed to a liquid and remains therein to reduce the purity of the alkoxide. The impurity returned to the alkoxide can be effectively removed by the stripping described above.

The concentrations of impurities in the purified alkoxide of the present invention obtained as described above are: 0.1 ppm or less and preferably 0.05 ppm or less for oxygen; 0.1 ppm or less and preferably 0.05 ppm or less for halogens and hydrogen halides; 10 ppm or less and preferably 1 ppm or less for alcohols; 100 ppm or less and preferably 10 ppm or less for the alkoxide polymer; 10 ppm or less and preferably 1 ppm or less for water; and 0.1 ppm and preferably 0.05 ppm or less for carbon dioxide.

The distillation and the stripping of the alkoxide as described above may be carried out, for example, by a purification apparatus having the construction shown in FIG. 1.

As shown in FIG. 1, the apparatus for purifying the alkoxide comprises a distilling apparatus and a stripping apparatus. The distilling apparatus for distilling a crude alkoxide 2 mainly comprises a distillation still 1 equipped with a heater 8, a distillation column 3, a condenser 4 and an intermediate tank 6. The stripping apparatus mainly comprises a stripping vessel 10 equipped with a heater 17, an ultrasonic vibrator 12, an inlet 13 for injecting a purified inert gas connected to a pipe 14 for supplying the purified inert gas, a reflux condenser 16 and a tank 18 for storing a purified alkoxide 19. An upper portion of the reflux condenser 16 is connected to a waste gas line 15. Pipes 9 for supplying a pressurized gas are disposed to transfer the distilled alkoxide 7 from the intermediate tank 6 to the stripping vessel 10 and to transfer the stripped alkoxide 11 from the stripping vessel 10 to a tank 18 for storing the purified alkoxide. Introduction and transfer of the gases and the liquids are controlled by valves 5, etc.

Figure 2:
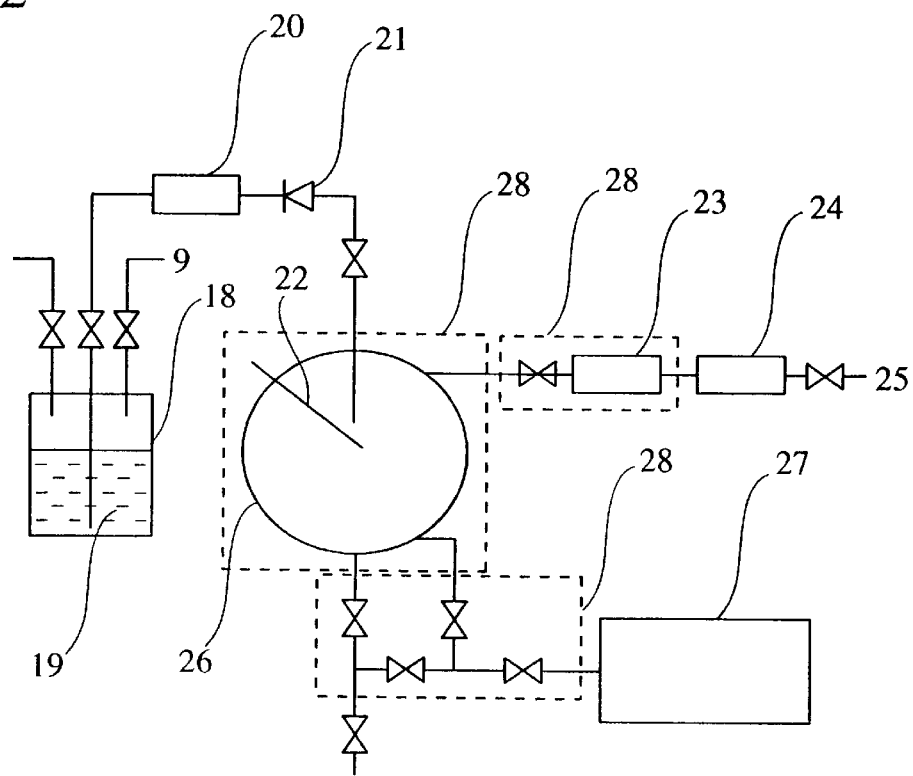
FIG. 2 is a schematic illustration showing an apparatus for vaporizing and supplying the purified alkoxide of the present invention.

The method of vaporizing and supplying the purified alkoxide of the present invention to an apparatus for producing semiconductors is not particularly limited so long as the purified alkoxide is supplied without degradation of its quality and the lost of its high purity. An example of the vaporizing-supplying apparatus is shown in FIG. 2. The purified alkoxide 19 in the tank 18 is introduced into a vaporizer 26 covered with a block heater 28 via a flow controller 20 and a check valve 21 and sprayed by an ultrasonic vibrator 22. The purified alkoxide thus sprayed is brought into contact with a heated carrier gas and vaporized in the vaporizer 26. The carrier gas is introduced into the vaporizer 26 via a carrier gas line 25, a flow controller 24 and a gas heater 23 covered with a block heater 28. The purified alkoxide thus vaporized is supplied to a CVD apparatus 27 via a line covered with a block heater 28 so that the alkoxide is not condensed or liquefied and used for forming thin films.

The present invention will be described more specifically with reference to the following examples. However, the present invention is not limited to the examples.

EXAMPLE 1

The apparatus as shown in FIG. 1 was used for purifying an alkoxide.

A quartz distillation apparatus for atmospheric distillation equipped with a 200 mm Widmer distillation column was used. A 1-liter stripping vessel made of electrolytically polished SUS 316 was equipped with an ultrasonic vibrator generating ultrasonic wave of 60 kHz with an output power of 1 W. Around the outer circumferential surface thereof, a heating jacket was disposed so as to heat the vessel or maintain the temperature of the vessel. An inlet pipe for injecting a purified inert gas was inserted into the stripping vessel so that the opening of the pipe was positioned near the bottom of the stripping vessel. A reflux condenser for cooling, liquefying and refluxing the vaporized alkoxide accompanied by the inert gas was attached at the upper portion of the stripping vessel. A pipe for a waste gas was attached to the reflux condenser. A tank for storing a purified alkoxide was made of electrolytically polished SUS 316 and had an inner volume of 1 liter.

A commercially available pentaethoxytantalum was analyzed by ion chromatography and found to contain about 1000 ppm of chlorine or hydrogen chloride. The result of quadrupole mass spectroscopy showed that this alkoxide contained about 950 ppm of oxygen. The results of ICP mass spectroscopy showed that this alkoxide contained 1 ppm or less, in total, of silicon, aluminum, boron, calcium, cobalt, iron, chromium, nickel, potassium, sodium, zinc, magnesium and manganese.

The above commercially available pentaethoxytantalum was distilled at atmospheric pressure. The concentration of chlorine or hydrogen chloride and the concentration of oxygen dissolved in the pentaethoxytantalum after the distillation were about 500 ppm and about 800 ppm, respectively. Then, 0.5 liter of the distilled pentaethoxytantalum was introduced into the stripping vessel via an intermediate tank under the pressure of purified argon. When the temperature of the pentaethoxytantalum introduced into the stripping tank reached 50° C. by heating, the ultrasonic vibration was started while passing the purified argon through the pentaethoxytantalum liquid from the inlet pipe at a flow rate of 500 cc/min. The temperature of the reflux condenser was kept at 25° C. by passing water as the coolant.

After 4 hours of the stripping, the stripping vessel was cooled by allowing it to stand, and then, the pentaethoxytantalum was transferred to the storage tank and obtained a purified pentaethoxytantalum.

The result of the analysis of the purified pentaethoxytantalum thus obtained by a gas chromatograph having a photoionization detector showed that the concentration of chlorine or hydrogen chloride decreased to 1.0 ppm and the concentration of oxygen decreased to 70 ppb. The results of ICP mass spectroscopy showed that the total concentration of silicon, aluminum, boron, calcium, cobalt, iron, chromium, nickel, potassium, sodium, zinc, magnesium and manganese decreased to $\frac{1}{10}$ or less of the total concentration before the purification.

EXAMPLE 2

A commercially available tetraethoxysilicon was analyzed by ion chromatography and found to contain about 800 ppm of chlorine or hydrogen chloride. The result of quadrupole mass spectroscopy showed that this alkoxide contained about 1200 ppm of oxygen The above tetraethoxysilicon was purified by using the purification apparatus as shown in FIG. 1 in the same manner as in Example 1. The tetraethoxysilicon after the distillation contained about 400 ppm of dissolved chlorine or hydrogen chloride and about 900 ppm of dissolved oxygen. After the distilled alkoxide was stripped by applying ultrasonic vibration while passing argon gas through the alkoxide, the concentration of chlorine or hydrogen chloride decreased to 1.0 ppm and the concentration of oxygen decreased to 120 ppb.

EXAMPLE 3

A commercially available tetraisopropoxytitanium was analyzed by ion chromatography and found to contain about 700 ppm of chlorine or hydrogen chloride. The result of quadrupole mass spectroscopy showed that this alkoxide contained about 1100 ppm of oxygen.

The above tetraisopropoxytitanium was purified by using the purification apparatus as shown in FIG. 1 in the same manner as in Example 1. The tetraisopropoxytitanium after the distillation contained about 650 ppm of dissolved chlorine or hydrogen chloride and about 1050 ppm of dissolved oxygen. After the distilled alkoxide was stripped by applying ultrasonic vibration while passing argon gas through the alkoxide, the concentration of chlorine or hydrogen chloride decreased to 0.8 ppm and the concentration of oxygen decreased to 150 ppb.

EXAMPLE 4

A vaporizing-supplying apparatus as shown in FIG. 2 was used.

The flow controller was composed of twin bellows pumps, and a check valve actuated by a pressure of 5 kgf/cm$^2$ was disposed at its outlet. The vaporizer was in a spherical shape having an outer diameter of 57 mm and an ultrasonic vibrator was disposed at the center thereof. A perforated plate of 0.5 mm thick having holes of a diameter of 3 mm arranged at a distance of 10 mm was horizontally disposed below the ultrasonic vibrator. An inlet of carrier gas was opened at an upper portion of the vaporizer so that a carrier gas was introduced into the vaporizer via a mass flow controller and a heater. The vaporizer was covered with a block heater having a shape corresponding to the contour thereof.

A thin film of tantalum oxide was formed on a substrate coated with titanium nitride by using the purified pentaethoxytantalum obtained in Example 1 in the manner described below.

The vaporizer and the passage from the vaporizer to a CVD apparatus were kept at 1 Torr and an argon carrier gas heated to 120° C. was supplied from the inlet into the vaporizer at a flow rate of 100 ml/min. The pentaethoxytantalum stored in the tank was transferred to the flow controller by the pressure of purified argon gas and then supplied to the vaporizer at a flow rate of 0.1 ml/min while applying ultrasonic vibration to spray and vaporize the pentaethoxytantalum. In the passage between the vaporizer and the CVD apparatus, a high purity oxygen gas was added at a rate of 600 ml/min and an argon diluent gas was added at a rate of 300 ml/min.

After mounting a titanium nitride-coated substrate in the CVD apparatus, the CVD apparatus was heated to 600° C. A gas containing the vaporized pentaethoxytantalum and oxygen prepared as described above was supplied to the CVD apparatus and a thin film of tantalum oxide was deposited on the titanium nitride-coated substrate. As a result of the measurement, it was confirmed that the thin film of tantalum oxide thus deposited had a thickness of 1000 to 2000 Å. The concentration of free $Cl_2$ in the deposited thin film of tantalum oxide was 1.0 ppm or less when measured by Auger electron spectroscopy.

EXAMPLE 5

By using the same vaporizing-supplying apparatus as used in Example 4 and the purified tetraethoxysilicon obtained in Example 2, a thin film of silicon oxide was formed on a silicon substrate in the manner described below.

The vaporizer and the passage from the vaporizer to a CVD apparatus were kept at 760 Torr and an argon carrier gas heated to 170° C. was supplied from the inlet into the vaporizer at a flow rate of 5000 ml/min. The tetraethoxysilicon stored in the tank was transferred to the flow controller by the pressure of purified argon gas and then supplied to the vaporizer at a flow rate of 1.0 ml/min while applying ultrasonic vibration to spray and vaporize the tetraethoxysilicon. In the passage between the vaporizer and the CVD apparatus, a high purity oxygen gas was added at a rate of 8000 ml/min and an argon diluent gas was added at a rate of 42000 ml/min.

The above gas containing the vaporized tetraethoxysilicon and oxygen gas was supplied to the CVD apparatus having a silicon substrate heated to 550° C., thereby depositing a thin film of silicon oxide on the silicon substrate. As a result of the measurement, it was confirmed that the thin film of silicon oxide thus deposited had a thickness of 1000 to 2000 Å. The concentration of free $Cl_2$ in the deposited thin film of silicon oxide was 1.0 ppm or less when measured by Auger electron spectroscopy.

EXAMPLE 6

By using the same vaporizing-supplying apparatus as used in Example 4 and the purified tetraisopropoxytitanium obtained in Example 3, a thin film of titanium oxide was formed on a silicon substrate in the manner described below.

The vaporizer and the passage from the vaporizer to a CVD apparatus were kept at 760 Torr and an argon carrier gas heated to 160° C. was supplied from the inlet into the vaporizer at a flow rate of 5000 ml/min. The tetraisopropoxytitanium stored in the tank was transferred to the flow controller by the pressure of purified argon gas and then supplied to the vaporizer at a flow rate of 0.5 ml/min while applying ultrasonic vibration to spray and vaporize the tetraisopropoxytitanium. In the passage between the vaporizer and the CVD apparatus, a high purity oxygen gas was added at a rate of 400 ml/min and an argon diluent gas was added at a rate of 35000 ml/min.

The above gas containing the vaporized tetraisopropoxytitanium and oxygen gas was supplied to the CVD apparatus having a silicon substrate heated to 680° C., thereby depositing a thin film of titanium oxide on the silicon substrate. As a result of the measurement, it was confirmed that the thin film of titanium oxide thus deposited had a thickness of 500 to 1000 Å. The concentration of free $Cl_2$ in the deposited thin film of titanium oxide was 1.0 ppm or less when measured by Auger electron spectroscopy.

COMPARATIVE EXAMPLE 1

A commercially available pentaethoxytantalum was purified in the same manner as in Example 1 except that ultrasonic vibration was not applied in the stripping step. The pentaethoxytantalum after the treatment contained about 470 ppm of dissolved chlorine or hydrogen chloride and about 900 ppm of dissolved oxygen. The results of ICP mass spectroscopy showed that the total concentration of silicon, aluminum, boron, calcium, cobalt, iron, chromium, nickel, potassium, sodium, zinc, magnesium and manganese decreased to $\frac{1}{10}$ or less of the total concentration before treating.

COMPARATIVE EXAMPLE 2

A commercially available tetraethoxysilicon was purified in the same manner as in Example 2 except that ultrasonic vibration was not applied in the stripping step. The tetraethoxysilicon after the treatment contained about 310 ppm of dissolved chlorine or hydrogen chloride and about 850 ppm of dissolved oxygen.

COMPARATIVE EXAMPLE 3

A commercially available tetraisopropoxytitanium was purified in the same manner as in Example 3 except that ultrasonic vibration was not applied in the stripping step. The tetraisopropoxytitanium after the treatment contained about 280 ppm of dissolved chlorine or hydrogen chloride and about 500 ppm of dissolved oxygen.

COMPARATIVE EXAMPLE 4

In the same manner as in Example 4, a thin film of tantalum oxide was deposited on a titanium nitride-coated substrate by using the purified pentaethoxytantalum obtained in Comparative Example 1. As a result of the measurement, it was confirmed that the thin film of tantalum oxide thus deposited had a thickness of 1000 to 2000 Å. The concentration of free $Cl_2$ in the deposited thin film of tantalum oxide was about 500 ppm when measured by Auger electron spectroscopy.

COMPARATIVE EXAMPLE 5

In the same manner as in Example 5, a thin film of silicon oxide was deposited on a silicon substrate by using the purified tetraethoxysilicon obtained in Comparative Example 2. As a result of the measurement, it was confirmed that the thin film of silicon oxide thus deposited had a thickness of 1000 to 2000 Å. The concentration of free $Cl_2$ in the deposited thin film of silicon oxide was about 300 ppm when measured by Auger electron spectroscopy.

COMPARATIVE EXAMPLE 6

In the same manner as in Example 6, a thin film of titanium oxide was deposited on a titanium nitride-coated substrate by using the purified tetraisopropoxytitanium obtained in Comparative Example 3. As a result of the measurement, it was confirmed that the thin film of titanium oxide thus deposited had a thickness of 500 to 1000 Å. The concentration of free $Cl_2$ in the deposited thin film of titanium oxide was about 300 ppm when measured by Auger electron spectroscopy.

As described above in detail, in accordance with the process of purifying an alkoxide of the present invention, the volatile impurities such as halogens, hydrogen halides, oxygen and carbon dioxide, which cause polymerization and degradation of the alkoxide and cannot be sufficiently removed by a conventional purification process by distillation, can be removed to extremely low concentrations.

What is claimed is:

1. A purified alkoxide having a concentration of residual oxygen of 0.15 ppm or less.

2. The purified alkoxide according to claim 1, wherein the alkoxide is purified by distilling a crude alkoxide to obtain a distilled liquid alkoxide and then stripping the distilled liquid alkoxide by applying ultrasonic vibration while passing an inert gas through the liquid alkoxide.

3. The purified alkoxide according to claim 1, wherein the alkoxide is represented by the following formula:

$$M(OC_nH_{2m+1})_n \text{ or } MO(OC_mH_{2m+1})_n$$

wherein M represents a metal, m represents an integer of 1 to 4 and n represents an integer of 3 to 5.

4. The purified alkoxide according to claim 3, wherein the alkoxide is a compound selected from the group consisting of tetraisopropoxytitanium, tetra-n-propoxytitanium, tetra-t-butoxyzirconium, tetra-n-butoxyzirconium, tetra-t-butoxyhafnium, tetramethoxyvanadium, trimethoxyvanadyl oxide, pentaethoxyniobium, pentaethoxytantalum, trimethoxyboron, triisopropoxyaluminum, tetraethoxysilicon, tetraethoxygermanium, tetramethoxytin, trimethoxyphosphorus, trimethoxyphosphine oxide, triethoxyarsenic and triethoxyantimony.

5. A process of purifying a crude alkoxide, comprising a step of distilling the crude alkoxide to obtain a distilled liquid alkoxide and a step of stripping the distilled liquid alkoxide by applying ultrasonic vibration while passing an inert gas through the liquid alkoxide.

6. The process according to claim 5, wherein the inert gas is passed through the liquid alkoxide in a manner such that the alkoxide is stirred by fine bubbles of the inert gas.

7. The process according to claim 5, wherein the inert gas is passed through the liquid alkoxide in an amount of 0.05 to 5 cc/sec per $cm^2$ of a plane perpendicular to a depth direction of the liquid alkoxide.

8. The process according to claim 5, wherein the ultrasonic vibration has a frequency of 30 to 200 kHz with an output power of 0.05 to 100 W per 1-liter alkoxide.

9. The process according to claim 5, wherein the alkoxide is represented by the following formula:

$$M(OC_mH_{2m+1})_n \text{ or } MO(OC_mH_{2m+1})_n$$

wherein M represents a metal, m represents an integer of 1 to 4 and n represents an integer of 3 to 5.

10. The process according to claim 9, wherein the alkoxide is a compound selected from the group consisting of tetraisopropoxytitanium, tetra-n-propoxytitanium, tetra-t-butoxyzirconium, tetra-n-butoxyzirconium, tetra-t-butoxyhafnium, tetramethoxyvanadium, trimethoxyvanadyl oxide, pentaethoxyniobium, pentaethoxytantalum, trimethoxyboron, triisopropoxyaluminum, tetraethoxysilicon, tetraethoxygermanium, tetramethoxytin, trimethoxyphosphorus, trimethoxyphosphine oxide, triethoxyarsenic and triethoxyantimony.

* * * * *